(12) United States Patent
Faccioli et al.

(10) Patent No.: US 10,426,866 B2
(45) Date of Patent: Oct. 1, 2019

(54) TERNARY MIXTURE FOR A BONE CEMENT AND METHOD FOR ITS REALISATION

(71) Applicant: TECRES S.p.A., Sommacampagna (Verona) (IT)

(72) Inventors: Giovanni Faccioli, Monzambano (IT); Renzo Soffiatti, Nogara (IT)

(73) Assignee: TECRES S.P.A., Sommacampagna (VR) (IT)

( * ) Notice: Subject to any disclaimer, the term of this patent is extended or adjusted under 35 U.S.C. 154(b) by 0 days.

(21) Appl. No.: 15/545,821

(22) PCT Filed: Feb. 12, 2016

(86) PCT No.: PCT/IB2016/050747
§ 371 (c)(1),
(2) Date: Jul. 24, 2017

(87) PCT Pub. No.: WO2016/128933
PCT Pub. Date: Aug. 18, 2016

(65) Prior Publication Data
US 2018/0015199 A1 Jan. 18, 2018

(30) Foreign Application Priority Data
Feb. 12, 2015 (IT) .................... 102015000006095

(51) Int. Cl.
*A61F 2/28* (2006.01)
*A61L 24/06* (2006.01)
*A61L 24/02* (2006.01)
*A61L 24/04* (2006.01)

(52) U.S. Cl.
CPC ........... *A61L 24/043* (2013.01); *A61L 24/046* (2013.01); *A61L 2430/02* (2013.01)

(58) Field of Classification Search
CPC .................................. C08L 33/08; C08L 33/10
See application file for complete search history.

(56) References Cited

U.S. PATENT DOCUMENTS

| 4,059,684 A * | 11/1977 | Gross | A61L 24/0015 |
| | | | 424/423 |
| 4,282,140 A | 8/1981 | Bousquet et al. | |
| 4,837,279 A | 6/1989 | Arroyo | |
| 2002/0001620 A1* | 1/2002 | Pienkowski | A61K 6/027 |
| | | | 424/486 |
| 2007/0191963 A1* | 8/2007 | Winterbottom | A61F 2/28 |
| | | | 623/23.5 |
| 2011/0054392 A1 | 3/2011 | Nies | |

FOREIGN PATENT DOCUMENTS

| EP | 1409032 | 4/2004 |
| WO | 02/058592 | 8/2002 |
| WO | 02/096474 | 12/2002 |
| WO | 2011/109684 | 9/2011 |

OTHER PUBLICATIONS

Nalawade et al. Chem Eng Sci, 62, 2007, 1712-1720.*
International Search Report dated May 10, 2016 for PCT/IB2015/050747 (2 pages).
International Preliminary Search Report dated Jul. 7, 2012 for PCT/IB2016/050747 (17 pages).
Po-Liang Lai, Chemical and Physical Properties of Bone Cement for Vertebroplasty, Biomed, Jul. 1, 2013, pp. 162-167.

* cited by examiner

*Primary Examiner* — Kyle A Purdy
(74) *Attorney, Agent, or Firm* — Tutunjian & Bitetto, P.C.

(57) ABSTRACT

Composition for an acrylic bone cement for surgical or orthopedic use including a solid phase including a ternary mixture, consisting of a polymethyl methacrylate (or PMMA) homopolymer, a methyl methacrylate-styrene (or MMA-styrene) copolymer and a methacrylate-methyl acrylate (or MMA-MA) copolymer, and a liquid phase containing at least an acrylic monomer.

33 Claims, No Drawings

TERNARY MIXTURE FOR A BONE CEMENT AND METHOD FOR ITS REALISATION

TECHNICAL FIELD OF THE INVENTION

The present invention relates to a composition comprising a ternary mixture for bone cements, implantable in the human body, such as a biomedical bone cement which can be used as bone adhesive in surgery for fixing joint prostheses and synthetic material in general, as bone filler, as material for making spacer devices, usable in the treatment in two revision stages of joint prostheses, etc. and to a bone cement obtained with such a composition.

The present invention further relates to a method for making a bone cement comprising the above ternary mixture and a kit comprising such a mixture and able to allow the surgeon to vary the viscosity of the bone cement thus obtained.

DESCRIPTION OF RELATED ART

Polymer-based bone cements have been used for a long time. One of the main uses of bone cements is to fix joint prostheses or implants in general to the bone tissue of a patient. Alternatively, bone cements are much used for making the whole or part of the spacer devices used to maintain the joint space during the revision stage of a prosthesis or to coat parts of prosthesis or implants.

Moreover, bone cements are usually used also as bone fillers, both in situations of damaged or osteoporotic bones or also for filling vertebrae.

The traditional chemical composition of bone cements is substantially as follows: a powder component and a liquid component. The powder component contains one or more polymers, mainly consisting of acrylates or methacrylates or homo- or co-polymers of the same (e.g. PMMA, polymethyl methacrylate). In addition, the powder component can contain powder radiopaque agents such as barium sulphate or zirconium dioxide, which are visible at x-rays and a radical initiator (usually comprising BPO or benzoyl peroxide).

The liquid component, instead, usually contains a reactive organic liquid such as the methyl methacrylate (MMA) monomer.

Activator or co-activator agents (usually NNDT or N—N dimethyl-para-toluidine) or stabilizers such as hydroquinone and derivatives thereof may be present.

The polymerization reaction of these components provides for the initiator and the co-activator to react, forming radicals which attack the chemical bonds of the monomer, favoring the elongation of the polymer chain. In parallel, the monomer or dissolves or solubilizes a portion of the polymer which initially leads to an increase in the viscosity of the mixture and causes an intimate connection between powder and liquid component.

Over time, typically from a few minutes to half an hour, the complete polymerization of the mixture takes place.

Since the basic plastic resin is transparent to x-rays, the bone cement must be made opaque by adding appropriate biocompatible inorganic substances. The opacity to X radiation of the elements increases substantially proportionally to the atomic weight of the same. Generally, especially for the heavier elements, also the toxicity increases. Bismuth in carbonate form, barium in sulphate form and zirconium in oxide form were and are commonly used in medicine as contrast elements of iodine type both in elemental and in bound form.

Using compounds such as salts or oxides, the radiopaque element constitutes only a part of the additive. For example, the metal is only 58% of barium sulphate, the balance being material substantially transparent to X radiation.

In known bone cements, such radio-opacifier materials generally consist of additions of barium sulphate or zirconium oxide, in amounts equal to about 10%-30% by weight of the dry polymer.

Patent application EP 1409032 by the same Applicant describes a radiopaque acrylic bone cement for orthopedic use comprising a solid phase consisting of a mixture comprising a polymer made from polymethyl methacrylate, a radical polymerization initiator and one or more substances opaque to x-rays, and of a liquid phase essentially consisting of a mixture of at least one monomer, one accelerator and one stabilizer.

SUMMARY OF INVENTION

One objects of the present invention is to improve the prior art.

Another object of the present invention is to provide a ternary mixture for bone cements and, in particular, a radiopaque acrylic bone cement having high mechanical resistance characteristics.

Another object of the present invention is to provide a ternary mixture for bone cements and, in particular, a radiopaque acrylic bone cement having variable viscosity characteristics.

Another object of the present invention is to provide a method of preparing a radiopaque acrylic bone cement, comprising a ternary mixture, which is simple to prepare.

According to one aspect of the invention, a radiopaque acrylic bone cement or a ternary mixture for bone cements is provided according to the present application.

According to a further aspect of the invention, a method for making a radiopaque acrylic bone cement or a ternary mixture for bone cements is provided according to the present application.

According to a further aspect of the present invention, a kit is provided, containing the above ternary mixture and further components, according to the present application, having the advantage of allowing the surgeon to change the viscosity of the resulting bone cement depending on the patient's needs.

The present application refers to advantageous embodiments of the invention.

DETAILED DESCRIPTION OF EMBODIMENTS OF THE INVENTION

The present invention relates to a ternary mixture for bone cements and, in particular, a radiopaque acrylic bone cement for surgical or orthopedic use.

Such bone cement comprises a solid phase and a liquid phase, in which the solid phase is at least partially dissolved in the liquid phase.

The solid phase of the bone cement comprises a ternary mixture formed by or having the following composition: three acrylic-based polymers, such as a polymethyl methacrylate (or PMMA) homopolymer, a methyl methacrylate-styrene (or MMA-styrene) copolymer and a methyl methyl methacrylate-methyl acrylate (or MMA-MA) copolymer.

These polymers are all soluble in the liquid phase that comprises an acrylic monomer.

Such a monomer acts as a solvent for the solid phase of the bone cement according to the present invention or, in particular, for the above ternary mixture.

The liquid phase comprises an acrylic monomer.

In one version of the invention, the liquid phase comprises an MMA (methyl methacrylate) monomer.

In another version, the liquid phase comprises a mixture of different acrylic monomers.

According to one example, the liquid phase may comprise MMA (methyl methacrylate) and/or BMA (butyl methacrylate) and/or EMA (ethyl methacrylate).

For example, in one version of the invention, the liquid phase substantially comprises 50% of MMA, 25% of BMA and 25% of EMA (by weight the total weight of the liquid phase).

In a further version of the invention, the acrylic component of the liquid phase substantially comprises 50% of MMA, 25% of BMA and 25% of EMA (by weight the total weight of the acrylic component).

Such compounds are acrylic monomers similar to MMA but with different hydrophilicity and polymerization rate and, in some respects, they may be preferable to MMA alone.

In a still further version of the invention, the liquid may not comprise MMA but only comprise BMA and/or EMA and/or a further acrylic monomer.

When MMA, BMA and EMA are present, they may be present in variable ratios by weight, wherein each component is variable from 1 to 98% on the total weight of the liquid phase or of the acrylic component, considering that the other two monomers substantially vary on a total considered substantially equal to 100%.

For example, in the presence of an MMA:BMA:EMA ratio of formula 98:1:1, there are 98% MMA, 1% BMA and 1% EMA.

Or, in the presence of an MMA:BMA:EMA ratio of formula 1:1:98, there are 1% MMA, 1% BMA and 98% EMA.

Still, a formula 50:45:5 means that there are 50% MMA, 45% BMA and 5% EMA, and so on.

Of course, the triad of monomers exemplified herein is one of the multiple possible combinations using the acrylic monomer molecules available. In order to be used in a bone cement or in the composition according to the present invention, such molecules must be acrylic monomers. Acrylic monomers can polymerize by a radical reaction promoted, for example, by peroxides.

The solubility of polymers in monomers is total, but the solubilization rate varies. The solubilization rate depends on various parameters, such as for example the molecular weight (MW) of the polymer. The higher the MW, the slower the solubilization rate. For example, a polymer with MW 400 solubilizes in more than twice the time compared to a polymer having MW 200. A further parameter that affects the solubilization rate is the polymer particle size: the finer they are, the earlier they solubilize and viscosize the environment. As regards copolymers, in addition to MW and particle size, the solubilization rate also depends on the relative ratio between the two monomers. For example, the MA-MMA copolymer with ratio 6:94 (namely comprising 6 parts of methyl acrylate and 94 parts of methyl methacrylate) has a solubility of about one third compared to the same copolymer but with a different ratio between the two monomers, i.e. for example 42:58. The MA-MMA copolymer may have a ratio of between 6:94 and 42:58.

The MA-MMA copolymer, in a further version of the invention, may have any relative ratio between MA and MMA.

Of course, the solubilization rate is extremely important for the speed of inducing the gel effect, i.e. that phase, prior to polymerization, in which the cement mass is still cold but is very viscous, with a consistency such as plasticine, in which manipulation is possible and very comfortable. Due to the easy manipulation, the cement can be easily placed in (even the most occluded) bone cavity without the risk that fragments or leaks are dispersed in the tissues with damage.

In other words, by suitably selecting the MW of the polymers and copolymers and by suitably selecting the copolymers with suitable relative ratios of the pair of monomers or of the components thereof, with the ternary mixture according to the present invention it is possible to obtain cements which, in less than a minute from the combination of the powder with the liquid, give a hyperviscous concrete that can be manipulated and is immediately applicable, as well as cements that remain highly fluid and thus injectable with syringes for hours, but that can never be manipulated.

The modulation degree of this aspect increases as the number of different polymers adopted increases and the ternary mixture according to the present invention achieves the best compromise.

In particular, the PMMA homopolymer, the MMA-styrene copolymer and the MMA-MA copolymer are in solid powder form and therefore make up the solid phase of the bone cement in question.

In one version of the invention, the solid phase of the bone cement comprises, as polymers or acrylic components, only the three polymers of the ternary mixture indicated above, that is to say, the PMMA homopolymer, the MMA-styrene copolymer and the MMA-MA copolymer.

In a further embodiment of the invention, the cement in question—prior to the polymerization—only comprises the following acrylic compounds: MMA monomer (in liquid phase), PMMA homopolymer, MMA-styrene copolymer and MMA-MA copolymer (in powder solid phase).

In a still further embodiment of the invention, the cement in question—prior to the polymerization—only comprises the following acrylic compounds: mixture of the above monomers (in liquid phase), PMMA homopolymer, MMA-styrene copolymer and MMA-MA copolymer (in powder solid phase).

The solid phase of the bone cement in question also comprises a catalyst or radical polymerization initiator.

The catalyst or polymerization initiator may comprise benzoyl peroxide or other suitable substances such as methyl ethyl ketone peroxide or other catalysts certified for human use.

The catalyst or polymerization initiator is present at a concentration of 0.2-0.6%, or up to 4% by weight on the total weight of the solid phase.

The solid phase of the bone cement in question may further comprise at least one radiopaque substance.

In one version of the invention, the solid phase of the bone cement in question may also comprise at least one coloring substance.

The at least one radiopaque substance may comprise barium and/or tungsten and/or tantalum salts in metallic form, compounds thereof or mixtures of the same, for example barium sulphate and/or bismuth oxide and/or zirconium oxide. Metal barium is toxic and barium sulphate is therefore exclusively used as it is insoluble and thus nontoxic. Barium chloride is instead soluble and therefore deadly.

Moreover, the particles which make up the at least one radiopaque substance may be coated with a coating layer made of a polymer compatible with the bone cement in question, such as an acrylic polymer based on PMMA.

One of the advantages of having such a coating layer is the fact of improving the homogeneity of the mixture or dispersion of the at least one radiopaque substance in the solid phase of the bone cement in question, or of improving the solubility thereof in the liquid phase.

Alternatively, the particles which make up the at least one radiopaque substance may be not coated.

The at least one radiopaque substance is present at a concentration of about 5-60% or about 20-40% by weight on the total weight of the solid phase; the proportion depends on the type of radiopacifying agent.

The at least one radiopaque substance in solid form is present in the form of particles larger than the nanometer size. Nanometric particles are not used as they may be toxic. Barium sulphate, for example, is very fine (size of about 1 micron) but it does not risk to be toxic. However, these particles aggregate and form "clusters" with are dimensionally variable from a few microns to several hundreds, and therefore it is difficult to determine the final size thereof.

A very useful radiopaque substance, in one version of the invention, is granulated barium sulphate, comprising granules of size between about 200 microns and about 500 microns. Granules give a better radiopacity by virtue of their section. Moreover, granules flow in the mixture and do not cause dosing problems. In a further version of the invention, the at least one radiopaque substance is in liquid form as an alternative or in addition to the solid form. In this case, the at least one radiopaque substance in liquid form may comprise iodine derivatives, for example known by the name IOMERON.

The liquid phase essentially consists, in addition to the MMA monomer or to the mixture of acrylic monomers, also of an accelerator and at least one stabilizer.

The concentration of the MMA monomer or of the mixture of acrylic monomers is equal to about 80-99.9% by weight on the total weight of the liquid phase.

In one version of the invention, the accelerator may comprise N,N,dimethylparatoluidine; the accelerator is present at a concentration equal to 0.4-3% by weight on the total weight of the liquid phase.

In one version of the invention, the stabilizer is hydroquinone or methyl-hydroquinone, at a concentration on the total weight of the liquid phase of 1-80 ppm or 10-150 ppm.

The bone cement according to the present invention may be admixed with improvers of the mechanical performance in general and, in particular, of the fatigue strength. Particularly advantageous is the incorporation of "graphene" in the form of lamellar or segmental semimicrostructures ranging in size from 0.02 to 1 micron. Using nanometric particles of graphene is intentionally avoided due to hypothetical toxic risks (nanoparticles migrate into the tissues and in the body fluids and can be found in lymph nodes).

Graphene is a material consisting of a monoatomic layer of carbon atoms (i.e. having a thickness equal to the size of a single atom but with multiple surface). Graphene has the mechanical strength of diamond and the flexibility of plastic.

The bone cement according to the present invention is porous and allows the release of pharmaceutical or medicinal substances possibly contained therein.

Such porosity, in one version of the invention, consists of interconnected pores.

In a further embodiment of the invention, the porosity consists of non-interconnected pores; this depends, for example, on other and any added auxiliary substances. For example, if water is added, an interconnected porosity is obtained. On the other hand, if an organic solvent with high vapor pressure is added, such as ethyl ether or pentane, a not interconnected porosity is obtained.

In one version of the invention, the pores occupy a volume, within the polymerized bone cement volume, ranging between 0.05% and 60%.

The bone cement in question therefore comprises one or more pharmaceutical or medicinal substances such as, for example, at least an antibiotic or a substance that facilitates the healing of the bone in question, or a pharmacologically active substance. The at least one pharmaceutical or medicinal substance may be comprised in the solid phase of the bone cement in question: in this case, the at least one pharmaceutical or medicinal substance is in the form of powder.

Alternatively, the at least one pharmaceutical or medicinal substance may be comprised in the liquid phase of the bone cement in question: in this case, the at least one pharmaceutical or medicinal substance may be in at least one of the following forms:
fine solid dispersed in a solvent, or
solid dissolved in a suitable solvent which forms an emulsion with the liquid phase (e.g. MMA)
liquid mixed with a second liquid, in which the two liquids are immiscible and, under stirring, give a fluid emulsion, or in the form of liquid solution.

In a still further version, the at least one pharmaceutical or medicinal substance may be comprised both in the solid and in the liquid phase of the bone cement in question: in this case, the at least one pharmaceutical or medicinal substance is both in the form of solid powder and in one of the above liquid forms.

In this case, the at least one pharmaceutical or medicinal substance in solid form may be different from that in liquid form.

According to an example of the present invention, the pharmaceutical or medicinal substance comprises at least an antibiotic, such as for example at least one organic antibiotic or gentamicin and/or vancomycin and/or clindamycin.

In this case, the bone cement comprises several types of pharmaceutical or medicinal substances. This possibility is however present also by mixing together different substances in solid form or different substances in liquid form, provided that the various substances do not neutralize each other.

The at least one pharmaceutical or medicinal substance is present at a concentration of up to 60% on the total weight of the solid phase or up to 60% on the total weight of the liquid phase of the bone cement in question.

If, for example, in one version of the invention, the pharmaceutical substance is TCP or HA hydroxyapatite, these substances may also be added at 60% by weight on the weight of the solid phase, i.e. 60 g TCP and 40 g of the polymer mixture.

The liquid phase, in one version of the invention, consists of 80% of MMA monomer (or monomer mixture), 1% of NNDT accelerator and 19% of water.

The ternary mixture according to the present invention corresponds, in one version of the invention, to about 40%-95% or about 45%-95% or about 50%-95% by weight on the total weight of the solid phase or between 59% and 80% by weight on the total weight of the solid phase.

Within this percentage of ternary mixture, the PMMA homopolymer, the MMA-styrene copolymer and the MMA-MA copolymer are present in the following ratios: 80:10:10 or all intermediates up to 10:10:80.

Moreover, in one version of the invention, the solid phase and the liquid phase are mixed in the following proportions: 2:1.

In one version of the invention, the PMMA homopolymer is present at a concentration equal to 60% on the total weight of the solid phase or of the ternary mixture.

In one version of the invention, the MMA-styrene copolymer is present at a concentration equal to 30% on the total weight of the solid phase or of the ternary mixture.

In one version of the invention, the MMA-MA copolymer is present at a concentration equal to 10% on the total weight of the solid phase or of the ternary mixture.

In one version of the invention, the PMMA homopolymer is present at a concentration equal to 60% on the total weight of the ternary mixture, the MMA-styrene copolymer is present at a concentration equal to 30% on the total weight of the ternary mixture and the MMA-MA copolymer is present at a concentration equal to 10% on the total weight of the ternary mixture.

As regards the particle size of the powders that make up the solid phase of the bone cement in question, the ternary mixture is as follows: the PMMA homopolymer has particle sizes of 0.1-300 microns, and/or the MMA-styrene copolymer has particle sizes of 0.1-300 microns and/or the MMA-MA copolymer has particle sizes of 0.1-300 microns.

The bone cement according to the present invention provides that the various components that make up the solid phase are homogeneously mixed together. In this way, when combining the solid phase with the liquid, resulting in the start of the polymerization and hardening of the bone cement, as homogeneous a dispersion as possible of the various components in the volume or the mass of the resulting bone cement is obtained.

Such homogeneous dispersion regards both the at least one pharmaceutical or medicinal substance and the at least one radiopaque substance. In this way, the characteristics of the resulting bone cement may be comparable in all areas of the bone cement itself.

The bone cement according to the present invention, depending on the purposes for which it is used, may be for example injected or applied to the site of interest by means of a spatula or other means suitable for use. In a still further version of the invention, the bone cement according to the present invention can be used, in a solidifiable fluid form, together with special molds, for the production of spacer or prosthetic devices or also of bone substitutes in general.

Such molding takes place externally to the human body, therefore it is a so-called extracorporeal molding.

In the injectable form, the bone cement according to the present invention can possibly be used in vertebroplasty to fill damaged vertebral bodies.

The composition according to the present invention may be used as a bone adhesive for example in surgery, for fixing joint prostheses or as synthetic material in general.

A further feature of the bone cement according to the present invention consists in the fact that its viscosity is variable and/or adjustable.

In this way, the bone cement according to the present invention can respond optimally to the specific needs of the surgeon, which depending on the surgical and anatomical needs of the patient, may need to have a bone cement having a greater or lesser viscosity of the same.

Such variable and/or adjustable viscosity depends on the specific composition of the bone cement in question or, in particular, on the ternary mixture that makes up the solid phase.

The variable and/or adjustable viscosity can be increased, in one version of the invention, due to the presence, in the composition of the bone cement according to the present invention, of viscosizing polymers or additives.

Such viscosizing polymers or additives, when present, are soluble in the liquid phase comprising the MMA monomer or the mixture of acrylic monomers, according to a slower or more complex or alternatively faster kinetic, compared to the polymers that make up the solid phase of the cement bone in question or, in particular, the ternary mixture thereof.

Therefore, in the presence of such viscosizing polymers or additives, the bone cement according to the present invention will be more viscous than the bone cement in the absence of the same; in this way, the risk—for the injectable bone cement—of leakage or loss of cement, for example, at a vertebral level, is reduced. At the same time, increasing the viscosity of the cement shortens the operating time window, so as to wait less time to obtain the hardening of the bone cement itself or the thickening (and thus the workability) of the cement itself.

Alternatively, a further method for varying the viscosity of the bone cement according to the present invention, for the same composition, is to make the particles that make up the solid phase thereof even smaller compared to the sizes described above. Such a size reduction can take place, for example, by grinding the solid phase to obtain a maximum diameter of the particles not greater than 30 microns, or not greater than 50 microns, depending on the needs.

In this way, the finer particles are more easily dissolved by the liquid phase comprising the monomer and the resulting bone cement or mixture is rapidly very viscous, almost solid.

In this way, that is to say, being able to adjust the viscosity of the composition according to the present invention the surgeon has, for the same composition, a more fluid bone cement that can reach more easily or quickly any points in the human body or may fill more easily or quickly any surgical sites.

For example, in one version of the invention, the viscosity measured 4 minutes after mixing of the various components, is between 200 and 300 Pa*s. In order to reduce the viscosity and make the value decrease to below 200 Pa*s, the bone cement will be very fluid and able to reach sites even apparently not easily accessible, in this case, the bone cement may be subject to leakage or losses.

From the point of view of the surgeon, the possibility of increasing the viscosity of the cement mixture can be very interesting. Therefore, giving the doctor the opportunity to increase the viscosity as desired is a very useful feature of the present invention.

The viscosizing polymers or additives in one version of the invention comprise at least one of the components of the ternary mixture indicated above. In this case, the particle size of the viscosizing polymers or additives may be smaller than that of the components of the ternary mixture.

In order to speed up the thickening of the resulting concrete (thus obtaining a greater solubilization rate that in the absence of viscosizing polymers or additives), the particle size of these compounds may be in the range of between 0.1 and 300 microns, or 0.5 microns to 200 microns or 0.5 microns to 50 microns, depending on the needs.

In a further version, the viscosizing polymers or additives may be different from the components of the ternary mixture indicated above. For example, it may be a polymer with a very high or instantaneous solubilization rate that is able to immediately make the mixture very viscous. In this case, there may be the risk of reducing the mechanical properties of the resulting cement. According to a further example, it is a high molecular weight copolymer. This polymer or additive in one version of the invention is formulated using the most soluble polymers and/or also ground or having particles of small size, to enhance their viscosifier power.

According to another version of the invention, the at least one viscosizing polymer or additive may comprise water or a saline solution or another solvent suitable for the purpose.

For example, an additive such as water or an aqueous solution is immiscible with the solvent or monomer present in the liquid component of the cement according to the present invention, and at the same time is able to greatly accelerate the viscosizing reactions of the polymer mixture.

Therefore, the viscosizing polymers or additives may be such due to their chemical nature and/or due to the small size of the particles that make them up.

Exemplary methods through which the particle size of the at least one viscosizing polymer or additive is reduced are: particle micronisation or grinding of the particles or other techniques able to reduce the size of the particles, or cryo-grinding or emulsification, etc.

The emulsification occurs by mixing the viscosizing polymer or additive in a suitable solvent, creating a sort of "milk" from which the emulsion is obtained.

For example, the present invention provides a kit in which, in addition to the above powders of the solid phase (usually present in a 40 g sachet of cement powder), a further amount of powders (e.g. a second 5 g sachet) of a viscosizing polymer or additive is optionally present.

Conversely, by increasing the viscosity above 300 Pa*s, for example with the use of the above viscosizing additives or polymers, the bone cement according to the present invention can be for example hand-applied with a spatula, where there is a need to avoid the risk of leakage or loss or where the surgeon deems it appropriate to act with such a concrete.

These viscosity values shall be construed as illustrative and generic values demonstrating the mechanism of action of the composition according to the present invention. Other viscosity values may be identified, depending on the specific anatomical or surgical needs or on the patient's needs.

The bone cement according to the present invention is essentially made by following the steps of providing a solid phase and a liquid phase as defined above, mixing the solid phase with the liquid phase so that the liquid phase completely wets the solid phase.

During the step of mixing the solid phase with the liquid phase, the ternary mixture that forms part of the solid phase begins to dissolve into the monomer that at least partly makes up the liquid phase.

The method of manufacture may provide the further steps of grinding or otherwise reducing the size of the particles that make up the solid phase in order to reduce the size of the particles that make it up or adding additional viscosizing polymers or additives.

The step of grinding or reducing the size of the particles takes place, according to one version of the invention, before mixing the solid phase with the liquid phase.

According to a further version of the invention, the step of adding additional viscosizing polymers or additives takes place prior to the step of mixing the solid phase with the liquid phase or after the same.

In a still further version of the invention, there may be both the step of grinding or reducing the size of the particles and that of adding additional viscosizing polymers or additives.

Once the solid phase has been mixed with the liquid one, the step of polymerization and hardening of the resulting bone cement begins.

The polymerization and hardening step may take place according to different times depending on the final components that make up the bone cement (e.g. if the additional viscosizing polymers are present or not) and/or on their size.

The above viscosity values that affect the polymerization and hardening timing and consequently the length of the time window in which the surgeon can work the resulting bone cement, are considered to be calculated at room temperature.

Finally, the surgeon may decide to vary or modulate the resulting bone cement viscosity by selecting the desired size of the particles of the solid phase components of the bone cement in question or deciding to add the viscosizing polymers, depending on his specific needs.

For example, if the surgeon has a bone cement with a viscosity not adequate for his needs and needs to make it more viscous, he can act according to at least two methods.

The first one is by adding at least one soluble viscosizing polymer or additive, possibly also having particles of average size of between 0.1 and 300 microns, which dissolves instantly and makes the cement less fluid.

According to a second method, the surgeon may add a viscosizing polymer or additive which is less soluble than the first method, but with an average particle sizes of between 0.1 or 0.5 and 50 microns: also in this case, the viscosizing polymer dissolves quickly and makes the concrete less fluid.

As seen, therefore, the bone cement according to the present invention or the ternary mixture which makes it up solves the drawbacks mentioned above with reference to the known acrylic cements. At the same time, the bone cement according to the present invention is biocompatible, visible to x-rays due to the presence of at least one radiopaque substance, has good mechanical properties of fatigue strength, due to the specific composition of the ternary mixture thereof, and at the same time, through devices that are quickly implemented, allows the surgeon to change or adjust the viscosity thereof, depending on the specific surgical, application and/or anatomical needs.

In fact, as mentioned, with the composition according to the present invention, the characteristics of the components of the ternary mixture (that is, the size of their particles, the molecular weights or the ratios between the various components of each copolymer, etc.) may be selected in order to adjust the viscosity of the resulting bone cement or to select the viscosity most suitable for the surgical needs (i.e. obtaining a more or less viscous bone cement).

Moreover, such a viscosity may be adjusted (e.g. increased) by adding viscosizing polymers or additives which, owing to their specific characteristics, can vary the viscosity of the mixture resulting from the combination of the solid phase and of the liquid one of the composition according to the present invention.

Several changes and variations may be made to the present invention thus conceived, all falling within the scope of the claims.

In particular, features described for one version of the invention may also be combined with other versions, without departing from the protection scope of the following claims.

The invention claimed is:

1. A composition for an acrylic bone cement for surgical or orthopedic use, wherein said composition comprises a solid phase comprising:
   a ternary mixture having the following composition: a polymethyl methacrylate (PMMA) homopolymer, a methyl methacrylate-styrene (MMA-styrene) copolymer and a methyl methacrylate-methyl acrylate (MMA-MA) copolymer, and
   a liquid phase comprising at least one acrylic monomer,
   further comprising at least one viscosizing polymer, wherein said at least one viscosizing polymer is soluble in said liquid phase and wherein said at least one viscosizing polymer has smaller particles than the particles making said ternary mixture,
   wherein said at least one viscosizing polymer comprises at least one of the components of said ternary mixture.

2. A composition for an acrylic bone cement for surgical or orthopedic use, comprising a solid phase comprising:
   a ternary mixture having the following composition: a polymethyl methacrylate (PMMA) homopolymer, a methyl methacrylate-styrene (MMA-styrene) copolymer and a methyl methacrylate-methyl acrylate (MMA-MA) copolymer, and
   a liquid phase comprising at least one acrylic monomer, wherein the liquid phase comprises a mixture of acrylic monomers such as methyl methacrylate (MMA) and/or butyl methacrylate (BMA) and/or ethyl methacrylate (EMA),
   further comprising at least one viscosizing polymer, wherein said at least one viscosizing polymer is soluble in said liquid phase, and wherein said viscosizing polymer has smaller particles than the particles making said ternary mixture,
   wherein said at least one viscosizing polymer comprises at least one of the components of said ternary mixture.

3. The composition according to claim 1, comprising at least a radiopaque substance in the form of powder or particles and/or at least a radiopaque substance in liquid form and/or at least a pharmaceutical or medicinal substance in solid form or at least a pharmaceutical or medicinal substance in liquid form.

4. The composition according to claim 1, wherein the liquid phase comprises methyl methacrylate (MMA) or a mixture of acrylic monomers such as methyl methacrylate (MMA) and/or butyl methacrylate (BMA) and/or ethyl methacrylate (EMA).

5. The composition according to claim 1, wherein said particle size of said at least one viscosizing polymer is between 0.1 and 300 micrometers (microns).

6. The composition according to claim 3, wherein said at least one radiopaque substance in the form of powder or particles comprises barium and/or tungsten and/or tantalum salts in metal form, compounds thereof, barium sulphate and/or bismuth oxide and/or zirconium oxide or granulated barium sulphate having granules sized between 200 micrometers (microns) and 500 micrometers (microns) or mixtures thereof, or wherein said at least one radiopaque substance has particles of the above compounds coated with a coating layer comprising a compatible polymer or an acrylic PMMA-based polymer and/or wherein said at least one radiopaque substance is in liquid form.

7. The composition according to claim 3, wherein said at least one radiopaque substance has a concentration of about 5-60% or about 20-40% by weight on the total weight of said solid phase.

8. The composition according to claim 1, wherein the MA-MMA copolymer has a ratio of 6:94, comprising 6 parts of methyl acrylate and 94 parts of methyl methacrylate, or a ratio of 42:58, comprising 42 parts of methyl acrylate and 58 parts of methyl methacrylate, or a ratio of between 6:94 and 42:58.

9. The composition according to claim 1, wherein said ternary mixture corresponds to about 40%-95% by weight on the total weight of said solid phase or between 45% and 95% by weight on the total weight of said solid phase or between 50% and 95% by weight on the total weight of said solid phase or between 59 and 80% by weight on the total weight of said solid phase.

10. The composition according to claim 1, wherein said PMMA homopolymer, MMA-styrene copolymer and MMA-MA copolymer are present in said ternary mixture according to ratios from 80:10:10 to 10:10:80 and/or wherein the PMMA homopolymer is present at a concentration equal to 60% on the total weight of said ternary mixture, said MMA-styrene copolymer is present at a concentration equal to 30% on the total weight of said ternary mixture and said MMA-MA copolymer is present at a concentration equal to 10% on the total weight of said ternary mixture.

11. The composition according to claim 1, wherein said solid phase comprises a catalyst or a radical polymerization initiator and/or wherein said liquid phase comprises an accelerator and at least one stabilizer.

12. The composition according to claim 11, wherein said catalyst or polymerization initiator comprises benzoyl peroxide or methyl ethyl ketone peroxide or other catalysts adapted to the purpose and for human use and/or wherein said catalyst or polymerization initiator is present at a concentration of 0.2-0.6% or up to 4% by weight on the total weight of said solid phase and/or wherein said accelerator comprises N,N,dimethyl-para-toluidine and/or wherein said accelerator is present at a concentration of 0.4-3% by weight on the total weight of said liquid phase and/or wherein said stabilizer comprises hydroquinone or methyl-hydroquinone, and/or wherein said stabilizer has a concentration on the total weight of said liquid phase of 1-80 ppm or 10-150 ppm.

13. The composition according to claim 1, comprising an agent improving the mechanical characteristics and/or the fatigue strength of the resulting bone cement, wherein such agent comprises graphene in the form of lamellar or segmental semimicrostructures having a size in the range from 0.02 micrometers to 1 micrometer (micron).

14. A method for making the composition for the acrylic bone cement for surgical or orthopedic use according to claim 1, comprising the following steps:
   providing a solid phase comprising a ternary mixture having the following composition: a polymethyl methacrylate (or PMMA) homopolymer, a methyl methacrylate-styrene (or MMA-styrene) copolymer and a methyl methacrylate-methyl acrylate (or MMA-MA) copolymer,
   providing a liquid phase comprising at least one acrylic monomer,
   mixing said solid phase and said liquid phase in order to obtain a resulting mixture, reacting said solid phase with said liquid phase or said resulting mixture in order to obtain a polymerization reaction of the components of said solid phase with said liquid phase, thereby obtaining a polymerized bone cement, selecting solubility and dimensions of at least one viscosizing polymer and adding said viscosizing polymer, which is soluble in said liquid phase, to said resulting mixture.

15. The method according to claim 14, comprising a step of adding to said solid phase and/or to said liquid phase at least one radiopaque substance and/or at least one pharmaceutical or a medicinal substance and/or comprising a step of adding graphene.

16. The method according to claim 14, wherein said viscosizing polymer is obtained by grinding or micronization of the particle of said viscosizing polymer or grinding of the particles of said viscosizing polymer or other techniques able to reduce the size of the particles, or cryo-grinding of said viscosizing polymer or emulsification of said viscosizing polymer in a suitable solvent.

17. The method according to claim 14, wherein said mixing step is carried out by mixing said liquid phase and said solid phase according to a ratio 2:1.

18. The method according to claim 14, comprising a step of grinding or micronizing or cryo-micronizing or emulsifying said solid phase to obtain particles having a maximum diameter not larger than 30 micrometers (microns) or not larger than 50 micrometers (microns).

19. A bone cement comprising the composition according to claim 1.

20. The bone cement according to the claim 19, comprising interconnected or not interconnected pores and/or comprising pores for a volume of between 0.05% and 60% of the volume occupied by said bone cement.

21. The bone cement according to claim 19, in injectable form, for use in the filling of damaged vertebral bodies in vertebroplasty.

22. The bone cement according to claim 19, whether in solid or solidifiable form, for use in the application of said bone cement in a bone cavity by a spatula or other means suitable for use.

23. Use of the bone cement according to claim 19, in solidifiable fluid form, for the extracorporeal formation of spacer or prosthetic devices or bone substitutes, through the use of appropriate molds.

24. A kit for making the composition for the bone cement for surgical or orthopedic use according to claim 1, comprising:
a first container containing a solid phase comprising a ternary mixture having the following composition: a polymethyl methacrylate (or PMMA) homopolymer, a methyl methacrylate-styrene (or MMA-styrene) copolymer and a methyl methacrylate-methyl acrylate (or MMA-MA) copolymer, optionally admixed with at least one radiopaque substance and/or at least one pharmaceutical or medicinal substance,
a second container containing a liquid phase containing at least an acrylic monomer,
optionally admixed with at least one radiopaque substance and/or at least one pharmaceutical or medicinal substance,
at least a third container comprising at least one viscosizing polymer and wherein said viscosizing polymer has smaller particles than the particles making said ternary mixture.

25. The composition according to claim 1, wherein said solid phase comprises, as single acrylic components, the components of said ternary mixture.

26. The composition according to claim 1, wherein said viscosizing polymer is admixed to a resulting mixture of said solid phase in said liquid phase so as to adjust the viscosity from said resulting mixture.

27. A method for making the composition for the acrylic bone cement for surgical or orthopedic use according to claim 1, comprising the following steps:
providing a solid phase comprising a ternary mixture having the following composition: a polymethyl methacrylate (or PMMA) homopolymer, a methyl methacrylate-styrene (or MMA-styrene) copolymer and a methyl methacrylate-methyl acrylate (or MMA-MA) copolymer,
providing a liquid phase comprising at least one acrylic monomer,
mixing said solid phase and said liquid phase in order to obtain a resulting mixture,
reacting said solid phase with said liquid phase or said resulting mixture in order to obtain a polymerization reaction of the components of said solid phase with said liquid phase, thereby obtaining a polymerized bone cement,
providing said liquid phase as a mixture of acrylic monomers such as methyl methacrylate (MMA) and/or butyl methacrylate (BMA) and/or ethyl methacrylate (EMA), wherein the concentration of said mixture of acrylic monomers is equal to 80-99.9% by weight on the total weight of the liquid phase.

28. The method according to claim 27, comprising a step of adding at least one viscosizing polymer, wherein said viscosizing polymer is soluble in said liquid phase.

29. The composition according to claim 1, wherein said particle size of said at least one viscosizing polymer is 0.5 micrometers (microns) to 200 micrometers (microns).

30. The composition according to claim 1, wherein said at least one viscosizing polymer comprises at least one of a polymer or copolymer different from those making up said ternary mixture.

31. The composition according to claim 1, wherein said at least one viscosizing polymer comprises at least one of a polymer or copolymer more soluble than the components of said ternary mixture.

32. The composition according to claim 1, wherein said at least one viscosizing polymer comprises at least one of the components of said ternary mixture.

33. The composition according to claim 1, said at least one viscosizing polymer comprises at least one of a polymethyl methacrylate (PMMA) homopolymer, a methyl methacrylate-styrene (MMA-styrene) copolymer and a methyl methacrylate-methyl acrylate (MMA-MA) copolymer.

* * * * *